(12) United States Patent
Kabakov

(10) Patent No.: US 8,694,081 B2
(45) Date of Patent: Apr. 8, 2014

(54) FETAL MONITORING SYSTEM AND METHOD

(75) Inventor: Serguei Kabakov, Laurel, MD (US)

(73) Assignee: General Electric Company, Schenectady, NY (US)

( * ) Notice: Subject to any disclaimer, the term of this patent is extended or adjusted under 35 U.S.C. 154(b) by 300 days.

(21) Appl. No.: 12/604,753

(22) Filed: Oct. 23, 2009

(65) Prior Publication Data

US 2011/0098586 A1 Apr. 28, 2011

(51) Int. Cl.
*A61B 5/0444* (2006.01)

(52) U.S. Cl.
USPC .......................................................... 600/511

(58) Field of Classification Search
USPC ................................................. 600/300, 511
See application file for complete search history.

(56) References Cited

U.S. PATENT DOCUMENTS

| | | | |
|---|---|---|---|
| 4,299,234 A | | 11/1981 | Epstein et al. |
| 4,489,726 A | | 12/1984 | Epstein et al. |
| 4,519,396 A | * | 5/1985 | Epstein et al. ................. 600/511 |
| 4,781,200 A | * | 11/1988 | Baker ........................... 600/483 |
| 4,945,917 A | | 8/1990 | Akselrod et al. |
| 5,170,791 A | | 12/1992 | Boos et al. |
| 5,372,139 A | | 12/1994 | Holls et al. |
| 5,666,959 A | | 9/1997 | Dean et al. |
| 6,245,025 B1 | | 6/2001 | Torok et al. |
| 7,333,850 B2 | | 2/2008 | Marossero et al. |
| 2010/0191118 A1 | | 7/2010 | Kabakov |

* cited by examiner

*Primary Examiner* — Rex R Holmes
(74) *Attorney, Agent, or Firm* — Andrus Intellectual Property Law, LLP

(57) ABSTRACT

A system and associated method include an AECG/PCG sensor configured to generate an AECG/PCG signal in response to a monitored fetal heart. The system also includes an US transducer configured to generate an US signal in response to the monitored fetal heart. The system also includes a computer configured to assess the quality of the AECG/PCG signal, and compare the assessed quality of the AECG/PCG signal with a selectable threshold value. The computer is also configured to disable the US transducer and process the AECG/PCG signal to provide a fetal heart rate estimate as long as the assessed quality of the AEC/PCG signal exceeds the selectable threshold value. The computer is also configured to enable the US transducer and process the US signal to provide a fetal heart rate estimate only if the assessed quality of the AEC/PCG signal is equal to or less than the selectable threshold value.

12 Claims, 2 Drawing Sheets

FETAL MONITORING SYSTEM AND METHOD

BACKGROUND OF THE INVENTION

The subject matter disclosed herein relates to a fetal monitoring system and method.

Fetal monitoring systems facilitate the process of monitoring the heart rate of an unborn child. Non-invasive fetal monitoring systems may rely on Doppler ultrasound (US), phonocardiography (PCG) or abdominal electrocardiography (AECG) technology. Portable fetal monitoring systems may, for example, be implemented to monitor a remotely located subject, when subject mobility is important, or to convenience a user.

One problem with portable and non-portable fetal monitoring systems relying on PCG or AECG technology is that they are generally less accurate than similar systems relying on US technology. One problem with portable fetal monitoring systems relying on US technology is that they rely on a portable power source such as a battery. Another problem with fetal monitoring systems relying on US technology is that they implement active technology (i.e., they emit US energy into the abdominal area) and are therefore less preferred by some users.

BRIEF DESCRIPTION OF THE INVENTION

The above-mentioned shortcomings, disadvantages and problems are addressed herein which will be understood by reading and understanding the following specification.

In an embodiment, a fetal heart rate monitoring system includes an AECG/PCG sensor configured to generate an AECG/PCG signal in response to a monitored fetal heart. The fetal heart rate monitoring system also includes an US transducer configured to generate an US signal in response to the monitored fetal heart. The fetal heart rate monitoring system also includes a computer configured to assess the quality of the AECG/PCG signal, and compare the assessed quality of the AECG/PCG signal with a selectable threshold value. The computer is also configured to disable the US transducer and process the AECG/PCG signal to provide a fetal heart rate estimate as long as the assessed quality of the AEC/PCG signal exceeds the selectable threshold value. The computer is also configured to enable the US transducer and process the US signal to provide a fetal heart rate estimate only if the assessed quality of the AEC/PCG signal is equal to or less than the selectable threshold value.

In another embodiment, a method includes generating an AECG/PCG signal in response to a monitored fetal heart, implementing a computer to assess the quality of the AECG/PCG signal, implementing the computer to compare the assessed quality of the AECG/PCG signal with a selectable threshold value, and processing the AECG/PCG signal to provide a fetal heart rate estimate as long as the assessed quality of the AEC/PCG signal exceeds the selectable threshold value. The method also includes generating a US signal in response to the monitored fetal heart, and processing the US signal to provide a fetal heart rate estimate only if the assessed quality of the AEC/PCG signal is equal to or less than the selectable threshold value.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
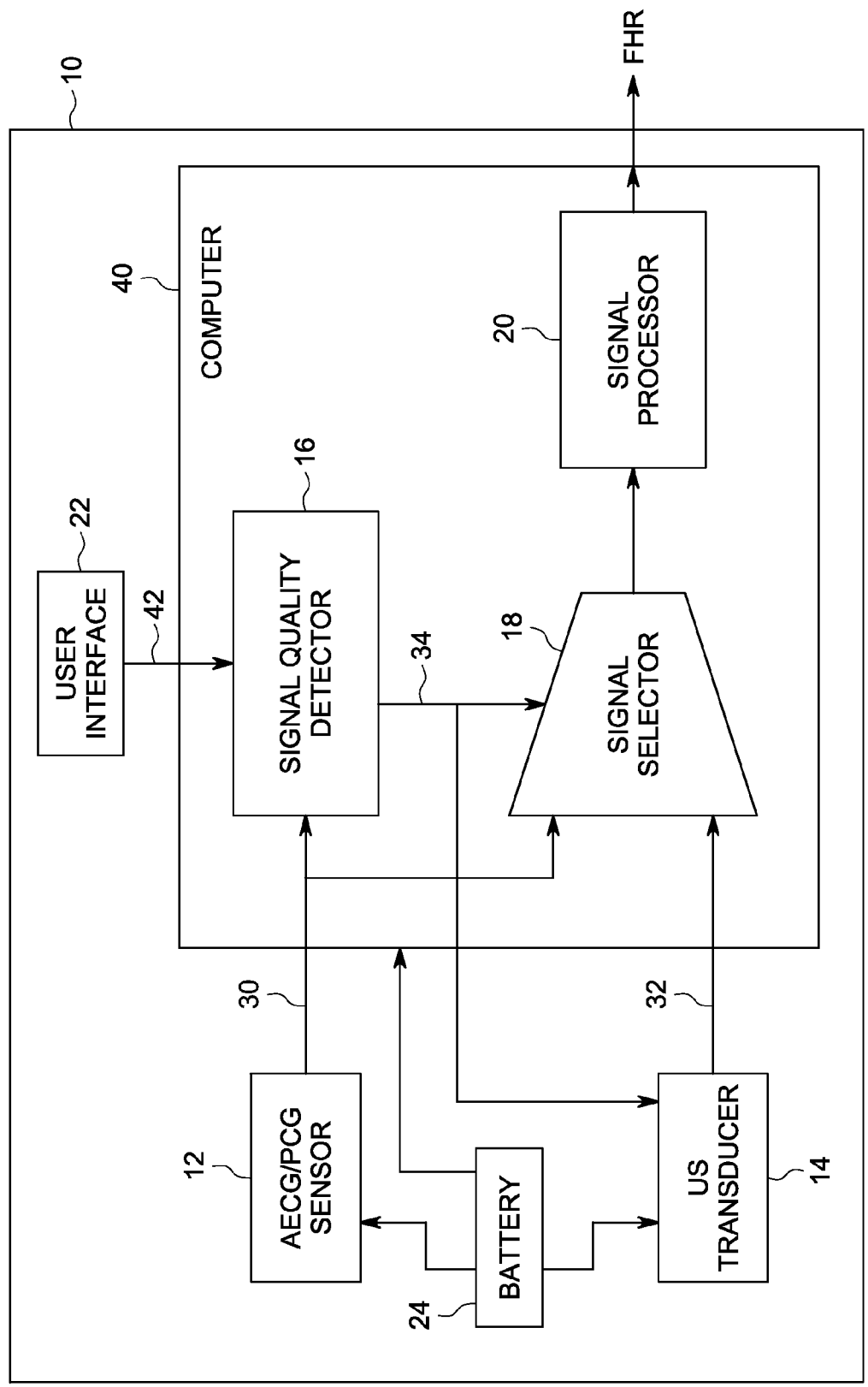
FIG. 1 is a schematic representation of a fetal heart rate monitoring system in accordance with an embodiment.

Referring to FIG. 1, a fetal heart rate (FHR) monitoring system 10 is shown in accordance with one embodiment. The FHR monitoring system 10 includes an abdominal electrocardiography (AECG) sensor and/or a phonocardiography (PCG) sensor that are hereinafter referred to as an AECG/PCG sensor 12. The FHR monitoring system 10 also includes a Doppler ultrasound (US) transducer 14, a signal quality detector 16, a signal selector 18, and a signal processor 20. According to the embodiment depicted in FIG. 1, the signal quality detector 16, the signal selector 18 and the signal processor 20 are all components of a computer 40, however alternate embodiments may implement individual components to provide similar functionality. The FHR monitoring system 10 will hereinafter be described as a portable monitoring system comprising an optional user interface 22 (e.g., a keyboard or touch screen) and a battery 24, however alternate monitoring system configurations and power supplies may be envisioned.

The AECG/PCG sensor 12 is connected to the signal quality detector 16, the signal selector 18 and the battery 24. The AECG/PCG sensor 12 implements abdominal electrocardiography to record, through the abdomen of a pregnant mother, the electrical activity of the fetal heart. The AECG/PCG sensor 12 also implements phonocardiography to record audible activity of the fetal heart (e.g., the sounds and murmurs produced as the fetal heart contracts). Electrocardiography and Phonocardiography are well known to those skilled in the art and therefore will not be described in detail. The AECG/PCG sensor 12 is configured to generate an AECG/PCG signal 30 based on recorded electrical activity and/or audible activity of the fetal heart. Accordingly, it should be appreciate that the AECG/PCG signal 30 may comprise an AECG signal and/or a PCG signal. The AECG/PCG signal 30 is transmittable from the AECG/PCG sensor 12 to both the signal quality detector 16 and the signal selector 18.

The US transducer 14 is connected to the signal quality detector 16, the signal selector 18 and the battery 24. The US transducer 14 implements an ultrasound-based technique to visualize, through the abdomen of a pregnant mother, the FHR waveform of an unborn fetus. Ultrasound-based diagnostic imaging is well known to those skilled in the art and therefore will not be described in detail. The US transducer 14 is configured to generate a US signal 32 that is transmittable to the signal selector 18. The US transducer 14 is also configured to receive a quality signal 34 comprising an operational status (i.e., either enabled or disabled) instruction from the signal quality detector 16.

The AECG/PCG sensor 12 can be sensitive to abdominal acoustic and electrical noise and therefore may provide a less precise FHR measurement as compared to the US transducer 14. Advantageously, however, the AECG/PCG sensor 12 is passive and is therefore preferred by some users as compared to the active US transducer 14. Additionally, the AECG/PCG sensor 12 consumes less power than the US transducer 14 and therefore prolongs the life of the battery 24.

The signal quality detector 16 is connected to the AECG/PCG sensor 12, the US transducer 14, and the signal selector 18. According to one embodiment, the signal quality detector 16 may assess signal quality based on a signal to noise ratio (SNR) calculation. As an example, the signal to noise ratio corresponding to the AECG/PCG signal 30 can be calculated according to the equation SNR=$\mu/\sigma$, where $\mu$ is the mean or expected value of the AECG/PCG signal 30, and $\sigma$ is an estimate of the standard deviation of the noise.

The following will provide a non-limiting exemplary method for obtaining the constituent variables $\mu$ and $\sigma$ for a SNR calculation of an AECG signal. The variable $\mu$ may be calculated as the average R-peak amplitude of a plurality of PQRST-complex waves derived from a fetal ECG signal, wherein the fetal ECG signal is extractable from a composite signal comprising a fetal heart signal; a maternal heart signal; and a maternal muscle noise signal. The variable $\sigma$ may be calculated as the standard deviation of noise beyond the PQRST-complex. Similarly, a non-limiting exemplary method for obtaining the constituent variables $\mu$ and $\sigma$ for a SNR calculation of a PCG signal will now be provided. The variable $\mu$ may be calculated as the average amplitude of a plurality of peaks of an autocorrelation function of the PCG signal. The variable $\sigma$ may be calculated as the standard deviation of the autocorrelation function beyond the peaks. Signal to noise ratio calculations for the purposes of assessing signal quality are well known to those skilled in the art and therefore will not be described in more detail.

According to one embodiment, the signal quality detector 16 receives a selectable signal quality threshold value 42 from the user interface 22. The signal quality detector 16 then compares a signal quality assessment with the threshold value 42 in order to generate the quality signal 34. The threshold value 42 is generally selected by a user to establish a minimally acceptable FHR measurement precision. The quality signal 34 indicates whether or nor a given signal quality assessment exceeds the threshold value 42. The quality signal 34 is transmittable from the signal quality detector 16 to both the US transducer 14 and the signal selector 18.

The signal selector 18 is connected to the AECG/PCG sensor 12, the US transducer 14, the signal quality detector 16, and the signal processor 20. The signal selector 18 is configured to receive the AECG/PCG signal 30 from the AECG/PCG sensor 12, the US signal 32 from the US transducer 14, and the quality signal 34 from the signal quality detector 16. The signal selector 18 is further configured to transmit either the AECG/PCG signal 30 or the US signal 32 to the signal processor 20 based on an analysis of the quality signal 34.

The signal processor 20 is connected to the signal selector 18. The signal processor 20 is configured to process the AECG/PCG signal 30 or the US signal 32 in order to produce a FHR measurement. AECG/PCG and US signal processing technology is well known to those skilled in the art and therefore will not be described in detail.

Having described the individual components of the FHR monitoring system 10, its operation will now be explained in more detail. When the FHR monitoring system 10 is initiated, the AECG/PCG sensor 12 transmits the AECG/PCG signal 30 to both the signal quality detector 16 and the signal selector 18. The signal quality detector 16 assesses the quality of the AECG/PCG signal 30 in the manner previously described or in accordance with any other known method. As long as the assessed quality of the AECG/PCG signal 30 remains greater than the user defined threshold value 42, the signal selector 18 will continue to transmit the AECG/PCG signal 30 to the signal processor 20 in order to generate the FHR measurement. This preferential reliance on the AECG/PCG signal 30 maximizes the use of passive AECG/PCG technology to measure FHR and also maximizes the life of the battery 70.

If the assessed quality of the AECG/PCG signal 30 becomes equal to or less than the user defined threshold value 42, the signal quality detector 16 will generate the quality signal 34 in order to enable the US transducer 14 and also to instruct the signal selector 18 to transmit the US signal 32. The signal processor 20 then processes the transmitted US signal 32 in order to generate the FHR measurement. In this manner, if the signal quality of the AECG/PCG signal 30 becomes inadequate for a given users needs, the FHR monitoring system 10 can automatically enable the US transducer 14 in order to maintain a highly precise FHR measurement.

Figure 2:
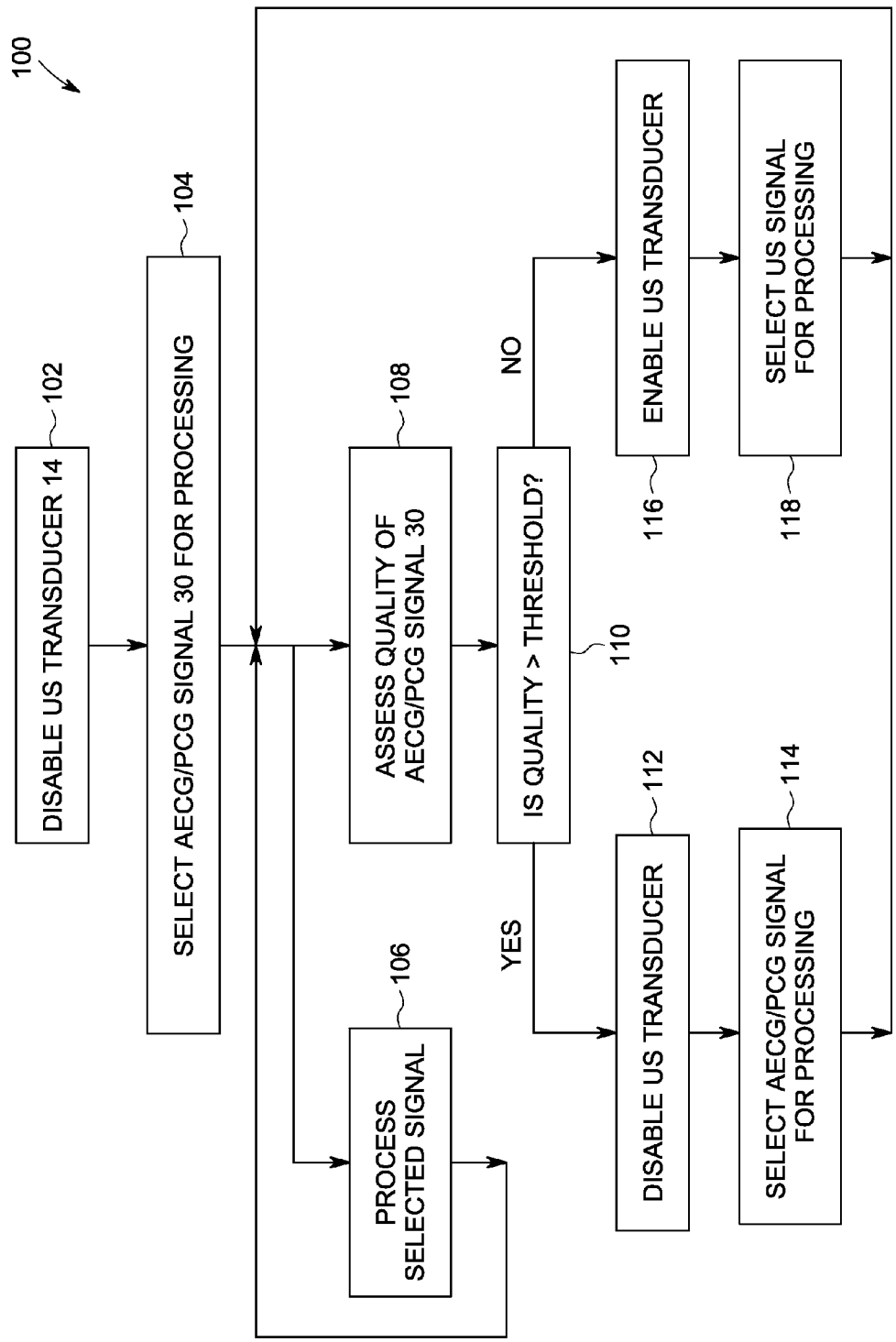
FIG. 2 is a flow chart illustrating a method in accordance with an embodiment.

Referring to FIG. 2, a method 100 will now be described in accordance with an embodiment. The method 100 comprises a plurality of steps 102-118. One or more of the steps 102-118 may be performed by the computer 40 of the FHR monitoring system 10 (shown in FIG. 1). The technical effect of the method 100 is to provide a FHR measurement maintained at a selectable level of precision with minimal reliance on US or other active monitoring techniques.

Referring to FIGS. 1 and 2, at step 102 of the method 100 the US transducer 14 is disabled. At step 104, the AECG/PCG signal 30 is selected for processing. It should be appreciated that by disabling the US transducer 14 and selecting the AECG/PCG signal 30 upon initiation, the method 100 relies on the AECG/PCG signal 30 by default such that use of the active US transducer 14 is minimized. After completing step 104, the method 100 generally simultaneously performs steps 106 and 108.

At step 106, a selected signal is processed to provide an FHR measurement. After completing step 106, the method 100 iteratively repeats step 106 and generally simultaneously performs step 108 that will subsequently be described in detail. During the first iteration of step 106, the selected signal is by default the AECG/PCG signal 30. The AECG/PCG signal 30 remains the selected signal and continues to be iteratively processed at step 106 until there is an indication that the resultant FHR measurement becomes insufficiently precise.

At step 108, the method 100 assesses the quality of the AECG/PCG signal 30. At step 108, the signal quality detector 16 may be implemented to assess the quality of the AECG/PCG signal 30 in the manner previously described or in accordance with any other known method. At step 110, the method 100 compares the quality of the AECG/PCG signal 30 to the user defined threshold value 42.

If, at step 110, the quality of the AECG/PCG signal 30 is greater than threshold value 42, the method 100 proceeds to step 112. At step 112, the US transducer 14 is disabled. At step 114, the AECG/PCG signal 30 is selected for processing. After completing step 114, the method 100 generally simultaneously repeats steps 106 and 108.

If, at step 110, the quality of the AECG/PCG signal 30 is less than or equal to threshold value 42, the method 100 proceeds to step 116. At step 116, the US transducer 14 is enabled. At step 118, the US signal 32 is selected for processing. After completing step 118, the method 100 generally simultaneously repeats steps 106 and 108.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A fetal heart rate monitoring system comprising:
   an abdominal electrocardiography sensor and a phonocardiography sensor configured in an abdominal electrocardiography/phonocardiography (AECG/PCG) sensor, wherein the AECG/PCG sensor is configured to generate an AECG/PCG signal in response to a monitored fetal heart, wherein the AECG/PCG signal includes an AECG signal or a PCG signal;
   an ultrasound (US) transducer configured to generate an US signal in response to the monitored fetal heart;
   a computer configured to:
      assess a quality of the AECG/PCG signal;
      compare the assessed quality of the AECG/PCG signal with a selectable threshold value;
      operationally disable the US transducer to stop generating the US signal and process the AECG/PCG signal to provide a fetal heart rate estimate as long as the assessed quality of the AECG/PCG signal exceeds the selectable threshold value; and
      enable the US transducer and process the US signal to provide a fetal heart rate estimate only if the assessed quality of the AECG/PCG signal is equal to or less than the selectable threshold value; and
   a battery configured to power the AECG/PCG sensor and the US transducer, wherein the operational disablement of the US transducer reduces a usage of the US transducer and increases a charge time of the battery.

2. The fetal heart rate monitoring system of claim 1, wherein the AECG/PCG sensor comprises an AECG sensor or a PCG sensor.

3. The fetal heart rate monitoring system of claim 1, wherein the AECG/PCG sensor comprises an AECG sensor and a PCG sensor.

4. The fetal heart rate monitoring system of claim 1, wherein the computer is configured to assess the quality of the AECG/PCG signal based on a signal to noise ratio calculation.

5. The fetal heart rate monitoring system of claim 1, further comprising a user interface connected to the computer.

6. The fetal heart rate monitoring system of claim 1, wherein the computer comprises a signal quality detector configured to produce a quality signal.

7. The fetal heart rate monitoring system of claim 6, wherein the computer comprises a signal selector connected to the signal quality detector, said signal selector configured to select one of the AECG/PCG signal and the US signal based on an analysis of the quality signal.

8. The fetal heart rate monitoring system of claim 7, wherein the computer comprises a signal processor connected to the signal selector, said signal processor configured to generate the fetal heart rate estimate based on one of the AECG/PCG signal and the US signal.

9. A method comprising:
   generating an abdominal electrocardiograph signal (AECG) or a phonocardiograph (PCG) signal from an abdominal electrocardiography/phonocardiography (AECG/PCG) sensor, wherein the AECG/PCG signal is in response to a monitored final heart, wherein the AECG/PCG sensor includes an AECG sensor and a PCG sensor;
   implementing a computer to assess a quality of the AECG/PCG signal;
   implementing the computer to compare the assessed quality of the AECG/PCG signal with a selectable threshold value;
   disabling operationally an ultrasound (US) transducer to not generate an US signal in response to the monitored fetal heart;
   processing the AECG/PCG signal to provide a fetal heart rate estimate as long as the assessed quality of the AECG/PCG signal exceeds the selectable threshold value; and
   enabling the US transducer and generating the US signal in response to the monitored fetal heart, and processing the US signal to provide a fetal heart rate estimate only if the assessed quality of the AECG/PCG signal is equal to or less than the selectable threshold value, wherein the operational disablement of the US transducer reduces a usage of the US transducer and increases a charge time of a battery.

10. The method of claim 9, wherein said generating an AECG/PCG signal comprises generating either an AECG signal or a PCG signal.

11. The method of claim 9, wherein said generating an AECG/PCG signal comprises generating both an AECG signal and a PCG signal.

12. The method of claim 9, wherein said assessing the quality of the AECG/PCG signal comprises calculating a signal to noise ratio of the AECG/PCG signal.

* * * * *